United States Patent

Lowrey

[11] 4,099,523
[45] Jul. 11, 1978

[54] THERAPEUTIC DEVICE
[75] Inventor: Thomas Patrick Lowrey, Kirkland, Ohio
[73] Assignees: Harry C. Walker; David E. Sukalac, ; part interest to each
[21] Appl. No.: 724,953
[22] Filed: Sep. 20, 1976
[51] Int. Cl.² ............................................. A61F 5/01
[52] U.S. Cl. .................................... 128/75; 128/78; 128/DIG. 23
[58] Field of Search ................ 128/75, 78, 76, 84 R, 128/84 C, DIG. 23, DIG. 20, 69

[56] References Cited
U.S. PATENT DOCUMENTS

| | | | |
|---|---|---|---|
| 1,589,670 | 6/1926 | Vartia | 128/75 |
| 1,986,273 | 1/1935 | Leffingwell | 254/93 R X |
| 3,075,521 | 1/1963 | Grassl | 128/75 |
| 3,285,244 | 11/1966 | Cottrell | 128/75 |

Primary Examiner—Robert W. Michell
Assistant Examiner—Michael H. Thaler
Attorney, Agent, or Firm—William N. Hogg

[57] ABSTRACT

A therapeutic device for applying controlled traction to the neck or lower back of a patient is disclosed. The device includes a pair of relatively rigid, hollow members telescopingly engaging each other. A bladder for the reception of air or other fluid is disposed within the members. The bladder has a stem to permit it to be filled with fluid to a controlled pressure. The fluid pressure acts on the sections tending to cause them to separate axially, but the rigid material prevents radial expansion. Thus, the device provides a controlled amount of traction in an axial direction without a choking radial component.

6 Claims, 4 Drawing Figures

THERAPEUTIC DEVICE

BACKGROUND OF THE INVENTION

This invention relates generally to therapeutic devices for applying traction, and more particularly, to therapeutic devices which allow for ambulatory use by the patient in which the amount of traction can be very closely controlled in a relatively simple manner.

In the treatment of many patient symptoms, especially symptoms involving the back and the neck, the preferred treatment includes the application of traction to the neck or back, and it is usually desirable to be able to control the amount of traction and vary the amount of traction applied. Normally, the control of traction at different levels is most easily accomplished when the patient is confined in bed so that the intricate devices for applying the exact amount of traction are available. Heretofore, however, it has not been feasible to closely control traction on ambulatory devices because of the relative complexity of the equipment involved and a need for close watch and calibration and the need for constant, professional attendance to the control of the amount of traction applied.

SUMMARY OF THE PRESENT INVENTION

According to the present invention, a traction or longitudinal separation device is provided which is comprised of a pair of telescoping sections, formed of a relatively rigid construction, which have a hollow interior in which is disposed a bladder or other type of inflatable member. When the bladder is inflated with air or other fluid, the pressure tends to generate a force which causes a separating, telescoping movement of the two sections responsive to the increase of pressure. The greater the pressure, the greater will be the force exerted in the separation movement. Hence, the amount of traction applied can be controlled by the fluid pressure supplied to the bladder.

DESCRIPTION OF THE PREFERRED EMBODIMENT

Figure 1:
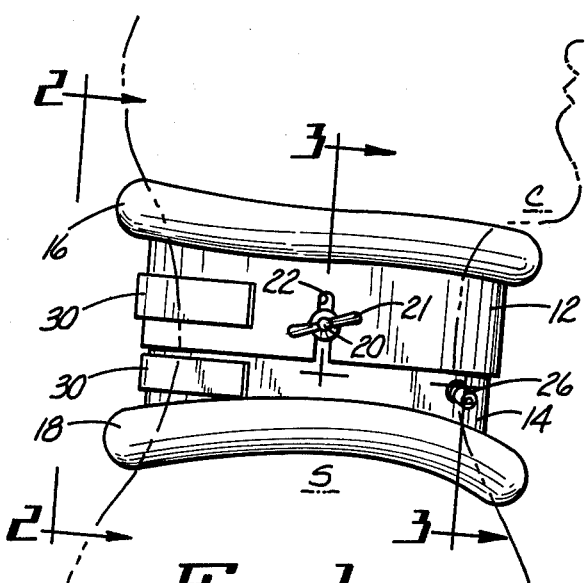
FIG. 1 is a side elevational view of a cervical collar, separation-traction device according to this invention, shown in place on a patient.
Figure 2:
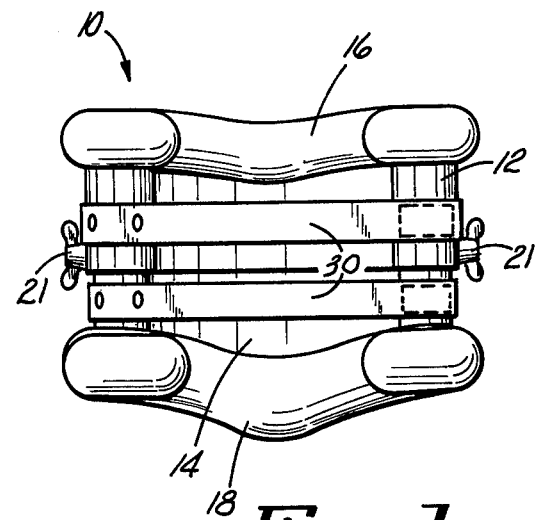
FIG. 2 is a rear-view of the device of FIG. 1 taken substantially along the plane designated by line 2—2 of FIG. 1.
Figure 3:
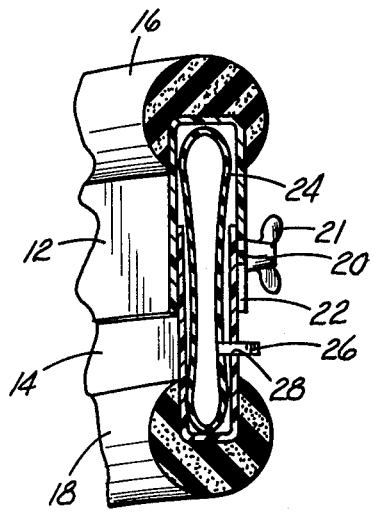
FIG. 3 is a longitudinal sectional view taken substantially along the plane designated by the line 3—3 of FIG. 2.

Referring now to the drawing, and for the present FIGS. 1–3, a therapeutic, separation-traction cervical device for applying traction in the neck area in the form of a cervical collar is shown and designated generally by the reference character 10. The device includes a superior section 12 and an inferior section 14, each of which is formed of a relatively rigid, relatively non-deformable material, preferably a hard plastic, and each is to generally a "U" shaped cross-section configuration as shown in FIG. 3, and arranged in a telescoping relationship. Padding 16 is provided at the top of the superior section 12 and padding 18 is supplied near the bottom of the inferior section 14, the padding 16 being provided to afford a cushion around the chin C and the lower portion of the skull, and the padding 18 to provide cushioning around the shoulder S of the wearer. The sections 12 and 14 are guided in their sliding relationship by means of threaded studs 20 on opposite sides of the inferior section 14 which project through elongated slots 22 on the opposite sides of the superior section 12. Wing nuts 21 are threaded onto the ends of each of the studs 20. Thus, the sections 12 and 14 are free to slide axially when the wing nuts 21 are loosened, but when the nuts 21 are clamped down, they will maintain the device tightly in its relatively adjusted position.

An elastomeric bladder 24 is disposed within the hollow interior of the telescope sections 12 and 14 and is essentially fluid tight and disposed to maintain fluid, preferably air, under pressure. Air is supplied to the interior of the bladder 24 by means of a air valve 26 which passes through an opening 28 formed in the inferior section 14.

The two sections 12 and 14 do not form a complete circle, but rather form the major portion of a circle (generally a horseshoe configuration) for encircling the neck area. They are open in the rear, however, so that the collar can be slipped over the neck. The collar then can be secured in place, preferably by means of straps 30 having a velcro or other type of fastening to allow the collar to be securely fastened around the neck.

In operation the wing nuts 21 are loosened and the straps 30 are loosened, and the collar is placed around the neck of the wearer. The straps 30 are then secured. The bladder 24 is then inflated with air through the valve 26. Air supplied to the bladder under pressure will cause the two sections 12 and 14 to move apart axially, responsive to the pressure and the expansion of the bladder within the interior. However, because the material forming the sections 12 and 14 is relatively non-deformable, i.e., it is substantially a rigid material, there will be no appreciable bulging of the material forming the sections, so there will not be any appreciable radial inward or outward movement of the device. Hence, the circumferential size of the device will not diminish upon inflation; rather, the inflation of the bladder and the pressure caused thereby will be confined essentially to axial separation movement of the two sections 12 and 14, generating separation-traction forces and not radially choking forces.

Once the desired degree of tractive force has been applied, the wing nuts 21 can be secured to maintain the collar in this position. The wing nuts 21 are not absolutely essential, and if the bladder were totally free of any leakage, the collar would remain in exactly the position with the exact pressure and force as set by the amount of air pressure in the bladder and not deviate therefrom. However, there may be a certain amount of loss of air pressure over a period of time or a tendency to lose pressure. Thus, it is desirable that once the separation-traction force on the patient has been set by the air pressure in the bladder, the wing nuts are secured to maintain the collar in this position. Thus, the wing nuts and the studs become a means for maintaining the device in the desired position as well as serving as a guide for movement of the two sections and maintaining the desired tractive force after the air bladder is used for initially setting and very closely controlling the amount of tractive force applied.

Figure 4:
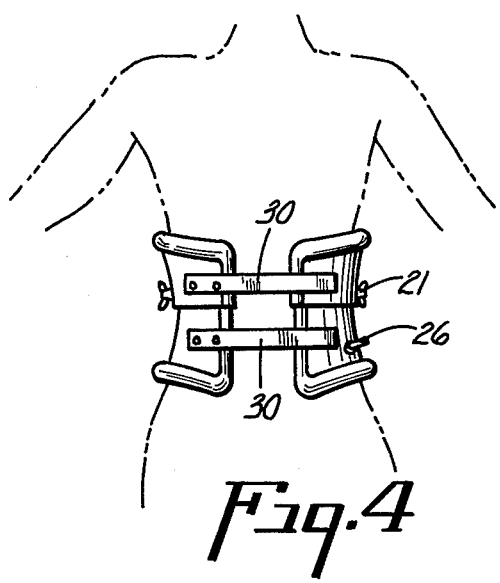
FIG. 4 is a rear-view of a separation-traction device according to this invention for providing traction in the lumbosacral area of the back.

Referring now to FIG. 4, a device very similar to that shown in FIGS. 1–3 is shown, but in this case, the shape of the device is slightly modified and the padding is somewhat rearranged so that it is suitable for the lumbosacral region to provide separation-traction thereto. In all other respects, though, including the telescoping rigid superior and inferior sections defining a hollow interior with an elastomeric bladder therein, and a valve therefor, this device is similar to that shown in FIGS. 1–3.

What is claimed is:

1. A therapeutic device for applying traction to a portion of the anatomy comprising,
    a pair of hollow substantially annular members, at least one of said members being hollow and U-shaped in cross section,
    said members being disposed in sliding telescoping relationship,
    said members having surfaces formed to at least partially encircle a selected portion of the anatomy,
    said members being formed of a relatively rigid, non-elastomeric material resistant to substantial deformation under pressure,
    fluid impervious bladder means disposed within the interior of the telescoped members,
    each of said members having internal bladder engaging surfaces,
    and means to allow fluid under pressure to be supplied to said bladder means,
    whereby fluid pressure in said bladder will generate a force against said bladder engaging surfaces urging sliding telescoping displacement without appreciable distortion of the members responsive to the fluid pressure in the bladder.

2. The invention as defined in claim 1 further characterized by padding means defining at least a portion of the surfaces which conform to the selected portion of the anatomy.

3. The invention as defined in claim 1 wherein said bladder is formed of an elastomeric material and adapted to receive air under pressure.

4. The invention as defined in claim 1 further characterized by guide means to control the direction of movement of said members.

5. The invention as defined in claim 1 further characterized by means to maintain any selected relative telescoping position at said members.

6. The invention as defined in claim 5 wherein said means to maintain any selected position includes threaded lug and nut means.

* * * * *